US008978737B2

United States Patent
Chang et al.

(10) Patent No.: US 8,978,737 B2
(45) Date of Patent: Mar. 17, 2015

(54) MOLDING SYSTEM

(71) Applicant: National Taiwan University of Science and Technology, Taipei (TW)

(72) Inventors: Fuh-Yu Chang, Taipei (TW); Ping-Tun Teng, Taipei (TW)

( * ) Notice: Subject to any disclaimer, the term of this patent is extended or adjusted under 35 U.S.C. 154(b) by 24 days.

(21) Appl. No.: 13/865,800

(22) Filed: Apr. 18, 2013

(65) Prior Publication Data

US 2014/0106020 A1 Apr. 17, 2014

(30) Foreign Application Priority Data

Oct. 2, 2012 (TW) .............................. 101136298 A

(51) Int. Cl.
| | |
|---|---|
| B29C 59/04 | (2006.01) |
| B29C 35/02 | (2006.01) |
| A61F 2/82 | (2013.01) |
| B29C 59/02 | (2006.01) |
| B29C 39/10 | (2006.01) |
| B29C 33/00 | (2006.01) |
| B29C 33/20 | (2006.01) |
| B29C 33/30 | (2006.01) |
| B29C 39/26 | (2006.01) |
| B29L 23/00 | (2006.01) |
| B29L 31/00 | (2006.01) |

(52) U.S. Cl.
CPC ................. *A61F 2/82* (2013.01); *B29C 59/021* (2013.01); *B29C 39/10* (2013.01); *B29C 35/02* (2013.01); *B29C 2059/023* (2013.01); *B29L 2023/007* (2013.01); *B29L 2031/7534* (2013.01); *B29C 33/005* (2013.01); *B29C 33/20* (2013.01); *B29C 33/308* (2013.01); *B29C 39/26* (2013.01)

USPC ........ 164/340; 29/895.33; 164/341; 249/155; 249/160

(58) Field of Classification Search
USPC ............ 29/895.3, 895.33; 249/152, 155, 156, 249/157, 160; 164/137, 339, 340, 341
See application file for complete search history.

(56) References Cited

U.S. PATENT DOCUMENTS

| | | | | |
|---|---|---|---|---|
| 873,138 | A | * | 12/1907 | Stults .............................. 249/17 |
| 892,592 | A | * | 7/1908 | Helm et al. ..................... 249/51 |
| 1,096,914 | A | * | 5/1914 | Hoadley .......................... 249/48 |
| 1,261,642 | A | * | 4/1918 | Neben ........................... 164/340 |
| 1,375,109 | A | * | 4/1921 | Rossiter et al. ................. 249/17 |
| 1,492,141 | A | * | 4/1924 | Neben ........................... 164/139 |
| 1,556,720 | A | * | 10/1925 | Saner .............................. 249/17 |
| 1,948,931 | A | * | 2/1934 | Mears ........................... 249/144 |

FOREIGN PATENT DOCUMENTS

| | | |
|---|---|---|
| JP | 1925-21648 | 12/1925 |
| JP | 2007261235 | 10/2007 |

* cited by examiner

*Primary Examiner* — Robert B Davis
(74) *Attorney, Agent, or Firm* — Richard C. Vershave; Foster Pepper PLLC

(57) ABSTRACT

The present invention discloses a molding system, more particularly, a shrinking type molding system comprising an outer mold, an inner mold and a first pattern layer. An adjustable gap is formed between the outer mold and the inner mold to contain a work piece therein. Furthermore, the work piece with a pattern structure on the surface thereof can be formed by the first pattern layer. The difference between the present invention and the prior art is that the molding system of the present invention is capable of optionally or simultaneously forming the pattern structure on the inner surface or the outer surface of the work piece, so as to solve the long last problem that not all the surfaces of the work piece could have the pattern structure thereon in the prior art.

10 Claims, 2 Drawing Sheets

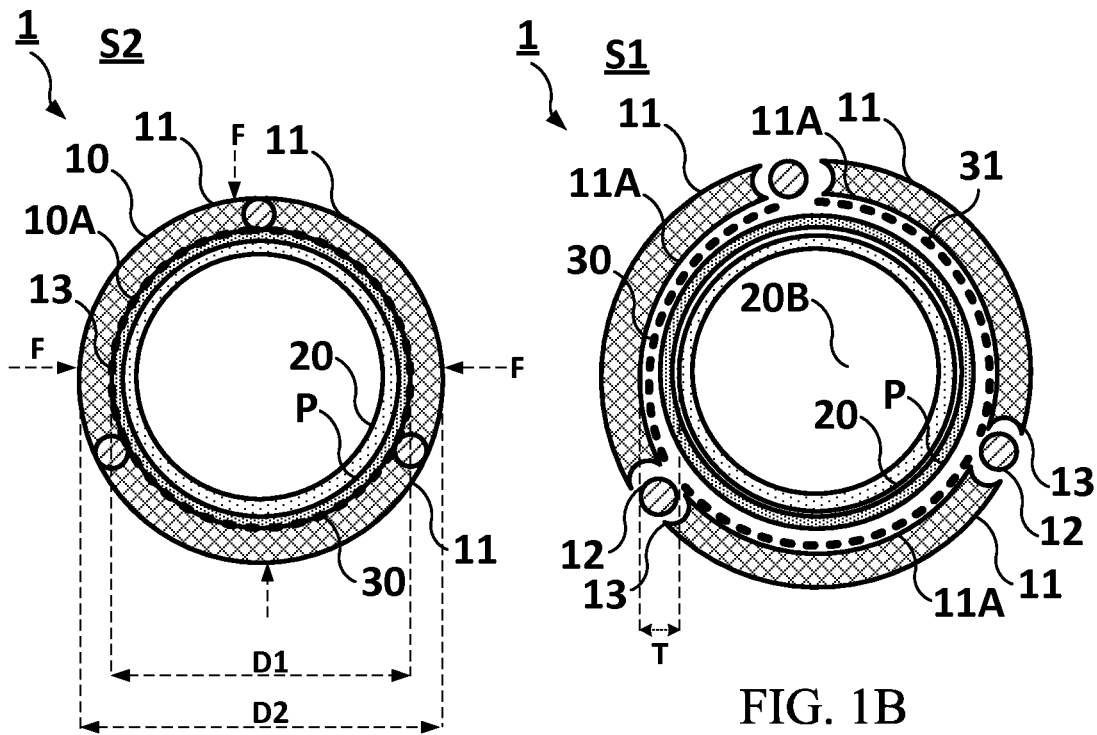
FIG. 1A
FIG. 1B
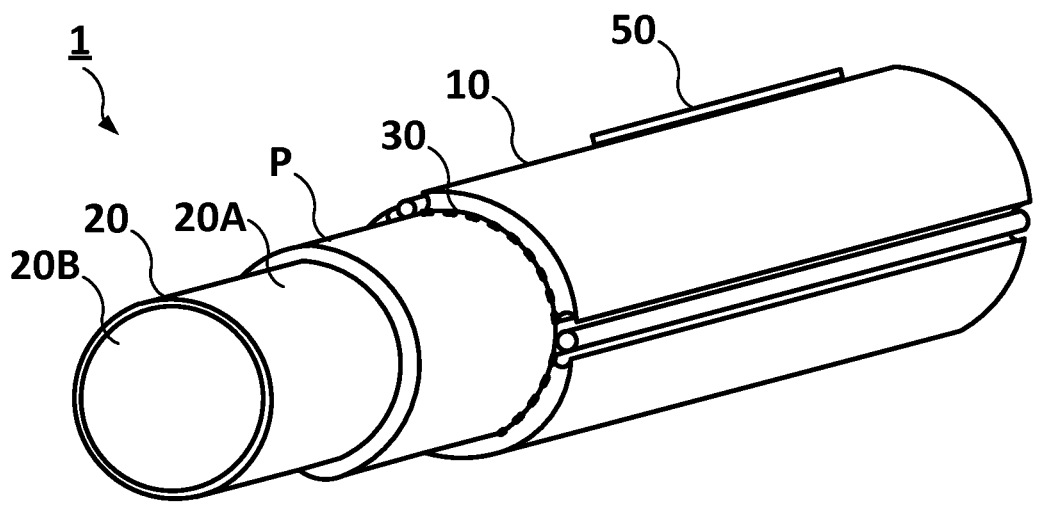
FIG. 1C

MOLDING SYSTEM

PRIORITY CLAIM

This application claims the benefit of the filing date of Taiwan Patent Application No. 101136298, filed Oct. 2, 2012, entitled "MOLDING SYSTEM," and the contents of which is hereby incorporated by reference in its entirety.

FIELD OF THE INVENTION

This invention relates to a molding system, and more particularly, to the shrinking type molding system capable of optionally or simultaneously forming a pattern structure on the inner surface and the outer surface of the work piece.

BACKGROUND OF THE INVENTION

In the prior art of manufacturing decomposable polymer coronary stent, several processes are used to form pattern structures on a tubular work piece. Those processes comprise carving the required structure on the surface of the work piece by the femtosecond laser; softening the target tube and fixing it on a rolling axle, and imprinting the surface of the target tube by a roller with pattern structure to form a corresponding surface structure on the tube; or fixing the target tube on a carrier, and milling the surface of the work piece to form a corresponding surface structure by CNC machine tool. Furthermore, an injection molding process can be used to melt and inject the materials into the mold with a specific shape to form the above-mentioned tube. However, the above processes in the prior art cannot be used for the high-precision product except the femtosecond laser. On the other hand, the femtosecond laser has shortcomings such as high technology level, high cost, slow process, and incapability in mass production. Besides, the femtosecond laser is unable to process the inner surface of the tubular work piece. If a great quantity and high-precision pattern is required on the inner surface of the coronary stent or the similar work piece, the process should be processing a 2D sheet material and then rolling up the 2D sheet material to a tube, and the process is complex and expensive. To lower down the technology level and the cost, simplify the process, and promote mass product ability of the tubular work piece processing system become important issues in the art.

SUMMARY OF THE INVENTION

One object of the present invention is to provide a molding system for processing a tubular work piece having an inner surface and an outer surface. The molding system comprises an outer mold, an inner mold, and a first pattern layer. The outer mold has a tubular shape and an inner wall. The inner mold is configured in the outer mold and has an outer wall facing the inner wall of the outer mold, and the shape of the outer wall can be corresponding to that of the inner wall. The first pattern layer is configured on the inner wall of the outer mold or the outer wall of the inner mold. The diameter of the outer mold can be adjusted to form an adjustable gap between the outer mold and the inner mold so as to enable the work piece to be placed into and be moved out from the gap.

The first pattern layer imprints on the inner surface or the outer surface of the work piece to form a corresponding pattern structure on the inner surface or outer surface of the work piece as an external force exerted on the outer mold to concentrically shrink the outer mold. Besides, a fluidic material can be poured into the gap and attached on the surface of the first pattern layer so as to form a corresponding pattern after solidifying.

The first pattern layer can be a metal thin film having a surface with a 3D pattern structure thereon, and the first pattern layer is fixed on the surface of the inner mold. The first pattern layer can be integrally formed of the inner mold. The outer mold comprises a plurality of submolds connected to each other by a plurality of fixing structure. The outer mold has an open state and a close state wherein the inner diameter of the outer mold in the open state is larger than that of the outer mold in the close state. Each submold has a sub inner wall respectively and the first pattern layer comprises a plurality of sub pattern layers that respectively formed on the sub inner walls of the submolds.

The molding system of the invention can comprise a second pattern layer placed opposite to the first pattern layer. The inner mold is a hollow tube having a passage for allowing a heating fluid to pass there through. The inner mold or the outer mold is mechanically connected to a heat source to acquire thermal energy via heat conduction.

As described above, the major difference between the present invention and the prior art is that the molding system of the present invention is capable of optionally or simultaneously forming the pattern structure on the inner surface or the outer surface of the work piece so as to solve the long last problem of the art.

On the advantages and the spirit of the invention, it can be understood further by the following invention descriptions and attached drawings.

BRIEF DESCRIPTION OF THE DRAWINGS

FIGS. 1A and 1B are sectional drawings illustrating a molding system before operating and in operation according to an embodiment of the invention.

FIG. 1C is a schematic drawing of the appearance of the molding system before operating according to an embodiment of the invention.

DETAILED DESCRIPTION

Figure 2:
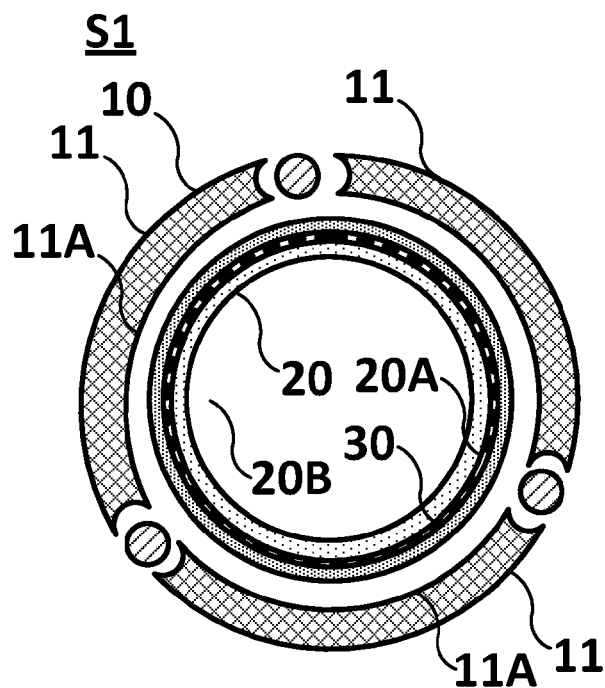
FIG. 2 is a sectional diagram illustrating the molding system according to another embodiment of the invention.

This invention discloses a molding system for providing a work piece having at least one pattern structure on the surface thereof. The difference between the present invention and the prior art is that the molding system is capable of optionally or simultaneously forming the pattern structure on the inner surface or the outer surface of a tubular work piece, or manufacturing a tubular work piece having the pattern structure.

Please refer to FIG. 1A to FIG. 1C. FIGS. 1A and 1B are sectional drawings illustrating a molding system before operating and in operation according to an embodiment of the invention. FIG. 1C is a schematic drawing of the appearance of the molding system before operating according to an embodiment of the invention. As shown in the figures, the molding system 1 for processing a tubular work piece P comprises an outer mold 10, an inner mold 20, and a first pattern layer 30 (shown by a dotted line). The followings will describe each element of the molding system 1 in detail.

In this embodiment, the outer mold 10 has a tubular shape and an inner wall 10A. The outer mold 10 is further formed by three or more submold 11. Each submold 11 respectively has a sub inner wall 11A, and the sub inner walls 11A together form the inner wall 10A, wherein the position of the arc center of each of the sub inner walls 11A and that of the circle center of the inner wall 10A are at the same point. The submolds 11 are connected to each other by fixing structures 12 respectively configured at two end of each submold 11. In detail, the side wall of each submold 11 has a groove 13 to contain a part of one of the tubular fixing structures 12. By this design, the outer mold 10 can be applied with an open state and a close state. In the close state, the side walls of one of the submold 11 contact those of other submolds 11 and the fixing structures 12 are buried in the grooves 13. In the open state, each submold 11 moves outward along the radial direction from the center, and is moveably connected to other submold 11 by the fixing structures 12. The outer diameter D2 and inner diameter D1 of the outer mold 10 in the open state are respectively larger than those in the close state. By the open state and the close state of the outer mold 10, the work piece P and the material thereof can get in or out the mold system 1 easily by the requirement of the user. It should be noted that the spreading and shrinking functions are not necessary in specific designs of the molding system 1 of the invention. To maintain the temperature of the outer mold 10 in processing the work piece P, the outer mold 10 can be mechanically connected to a heat source 50 to acquire thermal energy via heat conduction and maintain the temperature. The heat source 50 can be an electric hot plate, heating panel, or other similar heaters. The means of increasing the environment temperature in process can also achieve the same effect as the heat source 50.

The mold system 1 comprises the inner mold 20 configured in the outer mold 10. The inner mold 20 has an outer wall 20A facing the inner wall 10A of the outer mold 10, and the shape of the outer wall 20A is corresponding to that of the inner wall 10A. For example, the shapes of the outer wall 20A of the inner mold 20 and the inner wall 10A of the outer mold 10 are corresponding cylinders. The shape of the outer wall 20A or the inner wall 10A is not limited to the cylinder but any shape required by the user. In this embodiment, the inner mold 20 can be a hollow tube made by extruding, molding, or other one piece formed processes. The inner mold 20 can be applied with a passage 20B for a heating fluid to pass through, so as to provide thermal energy to the outer mold 10 for maintaining or raising the temperature. However, the invention is not just limited to the passage 20B. The inner mold 20 can be mechanically connected to a heat source 50 to acquire thermal energy via heat conduction according to the requirement of the user. The inner mold 20 in this embodiment is a rigid tube, but it is not a limitation. The inner mold 20 can be a balloon or a C-shaped leaf spring according to the requirement of the user to support the first pattern layer 30.

In practice, the materials of the outer mold 10 and the inner mold 20 can be metals having higher melting points than that of the work piece. For example, the outer mold 10 or the inner mold 20 can be made of carbon steel if the material of the work piece P is fluidic aluminum alloy, where the melting point of carbon steel is higher than that of aluminum alloy, so as to prevent the outer mold 10 or the inner mold 20 from softening and then influencing the precision of the system. It should be noted that the inner mold 20 can also have spreading and shrinking mechanisms similar as those of the outer mold 20.

The mold system 1 further comprises a first pattern layer 30 configured between the outer mold 10 and the inner mold 20 for defining the pattern structure of the surface of the work piece P. In this embodiment, the first pattern layer 30 is pre-configured on the inner wall 10A in one piece with the outer mold 10, so as to form the pattern structure on the outer surface of the work piece P. Besides, the first pattern layer 30 can be formed by a plurality of sub patterns 31 configured on the sub inner walls 11A of the submolds 11. In the close state of the outer mold 11, the sub patterns 31 can be combined together to form the first pattern layer 30 because the sub inner walls 11A of the submolds 11 are connected to each other. The sub patterns 31 can be arranged in order according to the requirement of the user.

It should be noted that although the first pattern layer 30 is formed on the inner wall 10A in one piece with the outer mold 10 in this embodiment, it is not a limitation in practice. The first pattern layer 30 can be a film or plate fixed on the inner wall 10A by sticking or other fixing means. Furthermore, the position where the first pattern layer 30 can be determined according to the requirement of the user but not limited to the inner wall 10A of the outer mold 10. Please refer to FIG. 2. FIG. 2 is a sectional diagram illustrating the molding system according to another embodiment of the invention. In this embodiment, the first pattern layer 30 can be configured or one piece formed on the outer wall 20A of the inner mold 20 for manufacturing the tubular work piece P which has the pattern structure on the inner surface thereof.

It should be noted that the sizes of the first pattern layer 30 and the corresponding pattern structure can be determined by the user. For example, the depth of the first pattern layer 30 can be designed at centimeter, micrometer, or nanometer scale. The minimum line width of the pattern on the first pattern layer 30 can arrive dozens nanometers. A specific process in needed when the size of the first pattern layer 30 is at micrometer or nanometer scale. For the precision of the system in the micrometer or nanometer scale processes, the thermal expansion of the outer mold 10 and the inner mold 20 should be regarded as well, The first pattern layer 30 at micrometer or nanometer scale can be directly formed on the outer wall 20A of the inner mold 20 or on the inner wall 10A of the outer mold 10 by MEMS (micro electromechanical systems) fabrication processes or laser machining process. On the other hand, the first pattern layer 30 can be formed independently and then configured on the outer wall 20A of the inner mold 20 or the inner wall 10A of the outer mold 10, and the process can comprise the following steps: forming a micrometer or nanometer scaled pattern on a silicon mold by light exposing, developing, or etching means; thermal transfer printing the pattern of a silicon mold onto a polycarbonate material to form a polycarbonate mold; coating a conducting layer on the surface of the polycarbonate mold, and then forming a flexible mold with the corresponding pattern structure on the polycarbonate mold, wherein the flexible mold can be made of nickel material; and, attaching the flexible mold on the inner surface of each of the submolds 11 to accomplish the first pattern layer 30. The submolds 11 and the sub patterns 31 have been described in the above paragraphs in detail, so they will not repeat here again. Besides, the above-mentioned process can be used for attaching the first pattern layer 30 on any position of the molding system 1 which is corresponding to one of the surfaces of the work piece P, and the unnecessary details will not repeat again, either.

Figure 3:
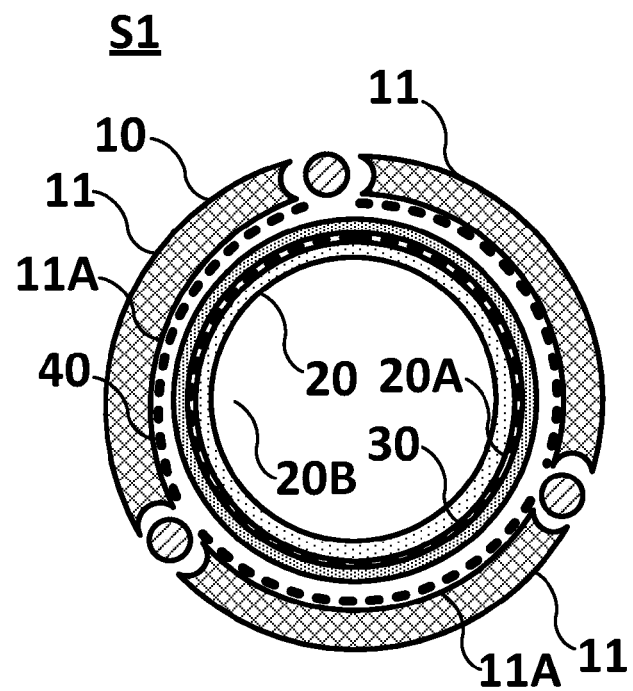
FIG. 3 is a sectional diagram illustrating the molding system according to another embodiment of the invention.

It should be noted that the present invention is not limited to single pattern layer in the molding system 1. The molding system 1 can further comprise a second pattern layer 40 corresponding to the first pattern layer 30 when the user wants to simultaneously form pattern structures on the inner surface and the outer surface of the work piece P. Please refer to FIG. 3. FIG. 3 is a sectional diagram illustrating the molding system according to another embodiment of the invention. As shown in FIG. 3, the first pattern layer 30 and the second pattern layer 40 are respectively configured on the outer wall 20A of the inner mold 20 and the inner wall 10A of the outer mold 10. The pattern, size, or other features of the second pattern layer 40 can be adjusted according to the requirement of the user, or can be just the same as or different from those of the first pattern layer 30. Also, the manufacturing process of the second pattern layer 40 can follow that of the first pattern layer 30 described in the above paragraphs, so that the unnecessary details will not repeat again.

After explaining the elements of the molding system 1, the operations of the molding system 1 will be described in the followings. The molding system 1 can be used for providing a work piece P with at least one pattern structure on a surface thereof by manufacturing the work piece P which has the pattern structure or forming the pattern structure on the surface of the work piece P.

The means for manufacturing the work piece P which has the pattern structure will be illustrate here. At first, the first pattern layer 30 can be configured on the inner wall 10A of the outer mold 10 or the outer wall 20A of the inner mold 20, and then configured the inner mold 20 in the outer mold 10 to make the inner wall 10A of the outer mold 10 facing the outer wall 20A of the inner mold 20. An adjustable gap T is formed between the outer mold 10 and the inner mold 20, wherein the size of the gap T is corresponding to the thickness of the work piece in direct ratio. The outer mold 10 is at the close state S2 at this time.

After the configuration of the inner mold 20 and the outer mold 10, a heat source 50 can be used for maintaining the temperature of the inner mold 20 and the outer mold 10 higher than the melting point or Curie point of the material of the work piece P to keep the flowability or formability of the material. The molding system 1 can further comprise a heating module to achieve the heating effect. After heating the inner mold 20 and the outer mold 10, the fluidic material can be poured into the gap T to fill the gap T to the full. The fluidic material fills the pattern of the first pattern layer 30 to define the pattern structure of the work piece P.

After filling the fluidic material in the gap T, the outer mold 10 and the inner mold 20 can be cooled down to solidify the fluidic material and obtain the solid work piece P. Accordingly, the pattern structure corresponding to the first pattern layer 30 can be formed on the surface of the work piece P. The inner mold 20 can be removed and the outer mold 10 can be turned to the open state S1 to take out the work piece P easily. The above process which manufactures the work piece P can be called as molding process for clarity. It should be noted that the work piece P has a fluid state and a solid state in the molding process, and it means that the work piece P can be made of the material capable of being melted or evaporated to the fluid. In detail, the material can be a liquid metal, a vapor metal, or other materials capable of being used in the molding process and having the fluid state after heating, such as polymer, glass, aluminum alloy, or carbon steel. The work piece P can be a coronary stent or other tubular work piece.

The molding system of the invention can be used for forming at least one pattern structure on the surface of the work piece P besides the molding process. The difference between this process and the molding process is that the work piece P has been pre-formed by the above-mentioned molding process or other means before forming the pattern structure on the surface thereof. The pre-formed work piece P can be placed into the gap T between the inner mold 20 and the outer mold 10 at the open state S1, and the first pattern layer 30 has been pre-configured on the inner wall 10A of the outer mold 10 or on the outer wall 20A of the inner mold 20. The inner mold 20 and the outer mold 10 are heated to soften the work piece P, and then an external force or a pressure is uniformly exerted on of the outer mold 10 toward the inner mold 20 to force the outer mold 10 shrinking to switch from the open state S1 to the close state S2. The outer mold 10 shrinks to make the first pattern layer 30 being pressed on the surface of the softened work piece P, and then the softened work piece P deforms correspondingly to the pattern of the first pattern layer 30. Accordingly, a pattern structure corresponding to the first pattern layer 30 is formed on the surface. The outer mold 10 can be spread to take out the processed work piece P for mold release. This process which forms the pattern structure on the work piece P can be called as imprinting process for clarity. For uniformly imprinting, the gas assisting imprinting process can be adopted in practice.

As described above, the major difference between the present invention and the prior art is that the molding system of the present invention is capable of optionally or simultaneously forming the pattern structure on the inner surface or the outer surface of the work piece, so as to solve the long last problem that not all the surfaces of the work piece could have the pattern structure thereon in the prior art.

Although the present invention has been illustrated and described with reference to the preferred embodiment thereof, it should be understood that it is in no way limited to the details of such embodiment but is capable of numerous modifications within the scope of the appended claims.

The invention claimed is:

1. A molding system for processing a tubular work piece having an inner surface and an outer surface, the molding system comprising:
   an outer mold having a tubular shape and an inner wall;
   an inner mold configured in the outer mold, the inner mold having an outer wall facing the inner wall of the outer mold; and
   a first pattern layer configured on the outer wall of the inner mold;
   wherein the diameter of the outer mold can be adjusted to form an adjustable gap between the outer mold and the inner mold so as to enable the work piece to be placed into and be moved out from the gap.

2. The molding system of claim 1, wherein the first pattern layer imprints on the inner surface or outer surface of the work piece to form a corresponding pattern structure on the inner surface or outer surface of the work piece as an external force exerted on the outer mold to concentrically shrink the outer mold.

3. The molding system of claim 1, wherein a fluidic material is poured into the gap and attached on the surface of the first pattern layer so as to form a corresponding pattern structure after solidifying.

4. The molding system of claim 1, wherein the first pattern layer is a metal thin film having a surface with a 3D pattern structure thereon.

5. The molding system of claim 1, wherein the first pattern layer is integrally formed on the surface of the inner mold.

6. The molding system of claim 1, wherein the outer mold comprises a plurality of submolds connected to each other by a plurality of fixing structures, and the outer mold has an open state and a close state where the inner diameter of the outer mold in the open state is larger than that of the outer mold in the close state.

7. The molding system of claim 1, further comprising a second pattern layer placed opposite to the first pattern layer.

8. The molding system of claim 1, wherein the inner mold is a hollow tube having a passage for allowing a heating fluid to pass there through.

9. The molding system of claim 1, wherein the inner mold or the outer mold is mechanically connected to a heat source to acquire thermal energy via heat conduction.

10. A molding system for processing a tubular work piece having an issue surface and an outer surface, the molding system comprising:
- an outer mold having a tubular shape, the outer mold comprising a plurality of submolds connected to each other by a plurality of fixing structures, each submold having a sub inner wall respectively;
- an inner mold configured in the outer mold; and
- a plurality of sub pattern layers, respectively configured on the sub inner walls;
- wherein the diameter of the outer mold can be adjusted to form an adjustable gap between the outer mold and the inner mold so as to enable the work piece to be placed into and be moved out from the gap.

* * * * *